US005466802A

United States Patent [19]

Panandiker et al.

[11] Patent Number: 5,466,802

[45] Date of Patent: Nov. 14, 1995

[54] DETERGENT COMPOSITIONS WHICH PROVIDE DYE TRANSFER INHIBITION BENEFITS

[75] Inventors: Rajan K. Panandiker, West Chester, Ohio; William C. Wertz, Lawrenceburg, Ind.; Larry J. Hughes, Cincinnati, Ohio

[73] Assignee: The Procter & Gamble Company, Cincinnati, Ohio

[21] Appl. No.: 150,644

[22] Filed: Nov. 10, 1993

[51] Int. Cl.[6] .................................................. C07D 251/20

[52] U.S. Cl. ................................ 544/193.2; 252/174.12; 252/174.15; 252/542; 252/544; 252/545; 252/546; 252/543; 252/547; 252/550; 252/551; 252/553

[58] Field of Search .................................. 252/547, 545, 252/546, 553, 194.12, 174.15, 544, 551, 550, 542, 543; 544/193.2

[56] References Cited

U.S. PATENT DOCUMENTS

| | | | |
|---|---|---|---|
| 4,144,226 | 3/1979 | Crutchfield et al. | 528/231 |
| 4,222,905 | 9/1980 | Cockrell, Jr. | 252/547 |
| 4,545,919 | 10/1985 | Abel | 252/174.18 |
| 4,764,302 | 8/1988 | Baker et al. | 252/301.23 |
| 4,772,404 | 9/1988 | Fox et al. | 252/8.8 |

FOREIGN PATENT DOCUMENTS

| | | | |
|---|---|---|---|
| 102923A1 | 3/1984 | European Pat. Off. | C11D 3/12 |
| 265257A2 | 4/1988 | European Pat. Off. | C11D 3/37 |
| 2814329 | 10/1979 | Germany | C11D 3/28 |
| 1348212 | 3/1974 | United Kingdom | C11D 3/28 |

OTHER PUBLICATIONS

Schuessler, U. *Proceedings of the Second World Conference on Detergents,* edited by A. R. Baldwin, American Oil Chemists' Society (1986), pp. 187–190.

Findley, W. R., "Fluorescent Whitening Agents for Modern Detergents", *JAOCS, vol. 65, No. 4,* (1988), pp. 679–683.

Jasperse, J. L., et al., "A System for Determining Optical Brighteners in Laundry Detergents by TLC and HPLC", *JAOCS, vol. 69, No. 7,* (1992), pp. 621–625.

Whalley, G. R., "Detergent Brighteners", *HAPPI,* (1993), pp. 82–87.

Findley, W. R. "Whitener Selection for Today's Detergents", *JAOCS, vol. 60, No. 7,* (1983), pp. 1367–1369.

*Primary Examiner*—Gary E. Hollinden
*Assistant Examiner*—Brian M. Burn
*Attorney, Agent, or Firm*—George W. Allen

[57] ABSTRACT

Disclosed are detergent compositions and methods which are suitable for washing colored fabrics in aqueous washing solution with little or no transfer of dye between fabrics. The compositions utilized comprise detersive surfactant, detergent builder, certain selected polymeric dye transfer inhibiting agents and certain selected hydrophilic optical brighteners. The polymeric dye transfer inhibiting agents are polyamine N-oxides such as poly(4-vinylpyridine-N-oxide), i.e., PVNO and/or copolymers of N-vinyipyrrolidone and N-vinylimidazole, i.e., PVPVI. The optical brighteners are selected from certain stilbenedisulfonic acid salts.

19 Claims, No Drawings

DETERGENT COMPOSITIONS WHICH PROVIDE DYE TRANSFER INHIBITION BENEFITS

FIELD OF THE INVENTION

This invention relates to laundry detergent compositions which can be used to wash dye-containing colored fabrics and which contain additives that inhibit dye transfer between fabrics during laundering operations.

BACKGROUND OF THE INVENTION

One of the most persistent and troublesome problem-causing events which arises during modem fabric laundering operations is the tendency of some colored fabrics to release dye into the laundering solutions. Such dye is then frequently transferred onto other fabrics being washed in the same aqueous washing solution.

One approach in attacking the dye transfer problem in laundering operations has been to complex or adsorb the fugitive dyes washed out of dyed fabrics before such dyes have the opportunity to become attached to other articles in the wash solution. Certain polymeric materials, for instance, have been suggested as being useful laundry detergent additives which can complex or adsorb fugitive dyes in aqueous washing solutions. For example Abel, U.S. Pat. No. 4,545,919; Issued Oct. 8, 1985 describes the use of carboxyl-containing polymers in fabric laundering operations. Waldhoffet al; DE-A-2 814 329, Published Oct. 11, 1979 discloses the use of N-vinyl-oxazolidone polymers and Cracco et al; GB 1,348,212; Published Mar. 13, 1974 discloses the use of 15–35% of a copolymer of polyvinylpyrrolidone and acrylic acid nitrile or maleic anhydride within a washing powder. Clements et al; EP-A-265 257; Published Apr. 27, 1988 describes detergent compositions comprising an alkali-metal carboxy-metal carboxymethylcellulose, a vinylpyrrolidone polymer and a polycarboxylate polymer.

Notwithstanding prior art attempts to solve the dye transfer problem during fabric laundering, there is a continuing need to identify detergent compositions, detergent composition additives and fabric laundering methods which are especially effective against dye transfer. Accordingly, it is an object of the present invention to provide detergent compositions which contain ingredients that eliminate or at least minimize dye transfer between fabrics when such compositions are used in fabric laundering operations.

It is a further object of the present invention to provide such especially effective dye transfer-inhibiting detergent compositions in either granular or liquid form.

It is a further object of the present invention to provide a method for laundering colored fabrics in aqueous washing solutions which are formed from the detergem compositions herein and which thereby contain materials that eliminate or at least minimize dye transfer between fabrics being washed therein.

SUMMARY OF THE INVENTION

The present invention is directed to laundry detergent compositions which provide especially effective inhibition of dye transfer between fabrics being laundered in aqueous washing solutions that are formed from these detergent compositions. Such detergent compositions comprise from about 1% to 80% by weight of a detersive surfactant, from about 0.01% to 80% by weight of a detergent builder component; from about 0.01% to 10% by weight of certain polymeric dye transfer inhibiting agent and from about 0.005% to 5% by weight of certain hydrophilic optical brightener compounds.

The polymeric dye transfer inhibiting agents can be polyamine N-oxide polymers, copolymers of N-vinylpyrrolidone and N-vinylimidazole or combinations of these polymers and copolymers. The hydrophilic optical brighteners used are those having the formula:

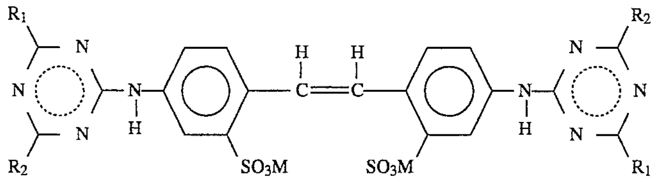

wherein $R_1$ can be anilino, N-2-bis-hydroxyethyl or NH-2-hydroxyethyl, $R_2$ can be N-2-bis-hydroxyethyl, N-2-hydroxyethyl-2-methylamino, morphilino, chloro or amino and M can be any salt-forming cation.

In its method aspects, the present invention provides a method for laundering colored fabrics with little or no dye transfer between fabrics taking place. Such a method comprises contacting such fabrics in an aqueous washing solution formed from an effective amount of the laundry detergent compositions herein.

DETAILED DESCRIPTION OF THE INVENTION

As noted, the laundry detergent compositions herein essentially contain detersive surfactant, detergent builder, certain polymeric dye transfer inhibiting agents and certain optical brighteners. Each of these essential components as well as optional ingredients for such compositions and methods of using such compositions are described in detail as follows:

A) Detersive Surfactant

The detergent compositions herein comprise from about 1% to 80% by weight of a detersive surfactant. Preferably such compositions comprise from about 5% to 50% by weight of this surfactant. Detersive surfactants utilized can be of the anionic, nonionic, zwitterionic, ampholytic or cationic type or can comprise compatible mixtures of these types. Detergent surfactants useful herein are described in U.S. Pat. No. 3,664,961, Norris, issued May 23, 1972, U.S. Pat. No. 3,919,678, Laughlin et al., issued Dec. 30, 1975, U.S. Pat. No. 4,222,905, Cockrell, issued Sep. 16, 1980, and in U.S. Pat. No. 4,239,659, Murphy, issued Dec. 16, 1980. All of these patents are incorporated herein by reference.

Of the surfactants, anionics and nonionics are preferred and anionics are most preferred. Such preferred anionic surfactants can themselves be of several different types. For example, water-soluble salts of the higher fatty acids, i.e., "soaps", are useful anionic surfactants in the compositions herein. This includes alkali metal soaps such as the sodium, potassium, ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Additional anionic surfactants which suitable for use herein include the water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are a) the sodium, potassium and ethanolamine alkyl sulfates, especially those obtained by sulfating the higher alcohols ($C_8$–$C_{18}$ carbon atoms) such as those produced by reducing the glycerides of tallow or coconut oil; b) the sodium, potassium and ethanolamine alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 ethoxylate moieties; and c) the sodium and potassium aikylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11-13}$ LAS.

Preferred nonionic surfactants are those of the formula $R^1(OC_2H_4)_n$ OH, wherein $R^1$ is a $C_{10}$–$C_{16}$ alkyl group or a $C_8$–$C_{12}$ alkyl phenyl group, and n is from 3 to about 80. Particularly preferred are condensation products of $C_{12}$–$C_{15}$ alcohols with from about 5 to about 20 moles of ethylene oxide per mole of alcohol, e.g., $C_{12}$–$C_{13}$ alcohol condensed with about 6.5 moles of ethylene oxide per mole of alcohol. Additional suitable nonionic surfactants include polyhydroxy fatty acid amides of the formula

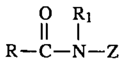

wherein R is a $C_{9-17}$ alkyl or alkenyl, $R_1$ is a methyl group and Z is glycityl derived from a reduced sugar or alkoxylated derivative thereof. Examples are N-methyl N-1-deoxyglucityl cocoamide and N-methyl N-1-deoxyglucityl oleamide. Processes for making polyhydroxy fatty acid amides are known and can be found in Wilson, U.S. Pat. No. 2,965,576 and Schwartz, U.S. Pat. No. 2,703,798, the disclosures of which are incorporated herein by reference.

B) Detergent Builder

The detergent compositions herein also comprise from about 0.1% to 80% by weight of a detergent builder. Preferably such compositions in liquid form will comprise from about 1% to 10% by weight of the builder component. Preferably such compositions in granular form will comprise from about 1% to 50% by weight of the builder component. Detergent builders are well known in the art and can comprise, for example, phosphate salts as well as various organic and inorganic nonphosphorus builders.

Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other suitable polycarboxylates for use herein are the polyacetal carboxylates described in U.S. Pat. No. 4, 144,226, issued Mar. 13, 1979 to Crutchfield et al, and U.S. Pat. No. 4,246,495, issued Mar. 27, 1979 to Crutchfield et al, both of which are incorporated herein by reference. Particularly preferred polycarboxylate builders are the oxydisuccinates and the ether carboxylate builder compositions comprising a combination of tartrate monosuccinate and tartrate disuccinate described in U.S. Pat. No. 4,663,071, Bush et al., issued May 5, 1987, the disclosure of which is incorporated herein by reference.

Examples of suitable nonphosphorus, inorganic builders include the silicates, aluminosilicates, borates and carbonates. Particularly preferred are sodium and potassium carbonate, bicarbonate, sesquicarbonate, tetraborate decahydrate, and silicates having a weight ratio of $SiO_2$ to alkali metal oxide of from about 0.5 to about 4.0, preferably from about 1.0 to about 2.4. Also preferred are aluminosilicates including zeolites. Such materials and their use as detergent builders are more fully discussed in Corkill et al, U.S. Pat. No. 4,605,509, the disclosure of which is incorporated herein by reference. Also, crystalline layered silicates such as those discussed in Corkill et al, U.S. Pat. No. 4,605,509, incorporated herein by reference, are suitable for use in the detergent composition of the invention.

C. Polymeric Dye Transfer Inhibiting Agents

The detergent compositions herein also comprise from about 0.01% to 10% by weight of certain types of polymeric dye transfer inhibiting agents. Preferably the detergent compositions herein comprise from about 0.05% to 0.5% by weight of these polymeric dye transfer inhibiting materials.

The selected dye transfer inhibiting polymeric materials can be certain polyamine N-oxide polymers, certain copolymers of N-vinylpyrrolidone and N-vinylimidazole or combinations of these types of materials. Each of these two polymer/copolymer types is described in greater detail as follows:

(i) Polyamine N-oxide Polymers

The polyamine N-oxide polymers suitable for use herein contain units having the structural formula:

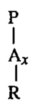

wherein P is a polymerizable unit to which a N-O group can be attached or the N-O group can form part of the polymerizable unit or the N-O group can be attached to both units; A is one of the following structures:

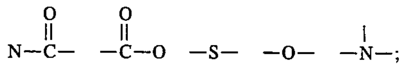

x is 0 or 1; and, R comprises aliphatic, ethoxylated aliphatic, aromatic, heterocyclic or alicyclic groups or any combination thereof to which the nitrogen of the N-O group can be attached or the N-O group is part of these groups.

The N-O group can be represented by the following general structures:

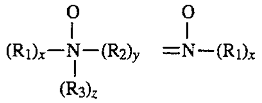

wherein $R_1$, $R_2$, $R_3$ are aliphatic, aromatic, heterocyclic or alicyclic groups or, combinations thereof; x, y and z are 0 or 1; and, the nitrogen of the N-O group can be attached or form part of any of the aforementioned groups. Further, the N-O group can be part of the polymerizable unit (P) or can be attached to the polymeric backbone or a combination of both.

Suitable polyamine N-oxides wherein the N-O group forms part of the polymerizable unit comprise polyamine N-oxides wherein R is selected from aliphatic, aromatic, alicyclic or heterocyclic groups. One class of such polyamine N-oxides comprises the group of polyamine N-oxides wherein the nitrogen of the N-O group forms part of the R group. Preferred polyamine N-oxides are those wherein R is a heterocyclic group such as pyrridine, pyrrole, imidazole, pyrrolidine, piperidine and derivatives thereof.

Another class of the polyamine N-oxides comprises the group of polyamine N-oxides wherein the nitrogen of the N-O group is attached to the R-group. Other suitable polyamine N-oxides are the polyamine oxides in which the N-O group is attached to the polymefizable unit. A preferred class of these polyamine N-oxides are the polyamine N-oxides having the general formula presented above wherein R is an aromatic, heterocyclic or an alicyclic group and the nitrogen of the N-O functional group is part of the R group. Examples of these classes are polyamine oxides wherein R is a heterocyclic compound such as pyrridine, pyrrole, imidazole and derivatives thereof.

Another preferred class of polyamine N-oxides are the polyamine oxides having the general formula presented above wherein R is an aromatic, heterocyclic or alicyclic group and the nitrogen of the N-O functional group is attached to the R group(s). Examples of these classes are polyamine oxides wherein R groups can be aromatic such as phenyl. Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers useful in the detergent compositions of the present invention typically have a ratio of amine to the amine N-oxide of 10:1 to 1:1,000,000. However, the number of amine oxide groups present in the polyamine oxide polymer can be varied by appropriate copolymefization or by an appropriate degree of N-oxidation. Preferably, the ratio of amine to amine N-oxide is from 3:1 to 1:1000000. The polymers useful in the detergent compositions of the present invention actually encompass random or block copolymers where one monomer type is an amine N-oxide and the other monomer type is an N-oxide.

The amine oxide unit of the polyamine N-oxides has a pKa<10, preferably pKa <7, more preferred pKa <6. The polyamine oxides can be obtained in almost any degree of polymerization. The degree of polymerization is not critical provided the material has the desired water-solubility and dye-suspending power. Typically, the average molecular weight is within the range of 500 to 1,000,000; more preferred 1,000 to 500,000; most preferred 5,000 to 100,000.

The most preferred polyamine N-oxide useful in the detergent compositions herein is poly(4-vinylpyridine-N-oxide) which has an average molecular weight of about 50,000 and an amine to amine N-oxide ratio of about 1:4. This preferred material can be abbreviated as "PVNO".

The polyamine N-oxides useful in the present invention can be synthesized by polymerizing the amine monomer and oxidizing the resulting polymer with a suitable oxidizing agent or the amine oxide monomer may itself be polymerized to obtain the desired polyamine N-oxide. Such reaction schemes are well known and within the scope of those persons skilled in the art.

(ii) Copolymers N-vinylpyrrolidone and N-vinylimidazole

The detergent compositions of the present invention may also utilize a copolymer of N-vinylpyrrolidone and N-vinylimidazole (also abbreviated herein as "PVPVI"). It has been found that copolymers of N-vinylpyrrolidone and N-vinylimidazole can provide excellent dye transfer inhibiting performance when utilized in the compositions of this invention.

In a preferred embodiment, the copolymer of N-vinylpyrrolidone and N-vinylimidazole polymers has an average molecular weight range from 5,000 to 1,000,000, more preferably from 5,000 to 200,000. A highly preferred copolymer for use in detergent compositions according to the present invention has an average molecular weight range from 5,000 to 50,000, more preferably from 8,000 to 30,000 and, most preferably from 10,000 to 20,000. The average molecular weight range is determined by light scattering as described in Barth J. H. G. and Mays J. W. Chemical Analysis Vol 113. "Modem Methods of Polymer Characterization", the disclosure of which is incorporated herein by reference.

The copolymers of N-vinylpyrrolidone and N-vinylimidazole useful in the present invention can have a molar ratio of N-vinylimidazole to N-vinylpyrrolidone from 1:1 to 0.2:1, more preferably from 0.8:1 to 0.3:1, most preferably from 0.6:1 to 0.4:1. It should be understood that the copolymer of N-vinylpyrrolidone and N-vinylimidazole can be either linear or branched.

D) Optical Brightener

The detergent compositions herein also essentially contain from about 0.005% to 5% by weight of a certain type of hydrophilic optical brightener. Preferably the compositions herein will comprise from about 0.01% to 1% by weight of this optical brightener.

The hydrophilic optical brighteners useful in the present invention are those having the structural formula:

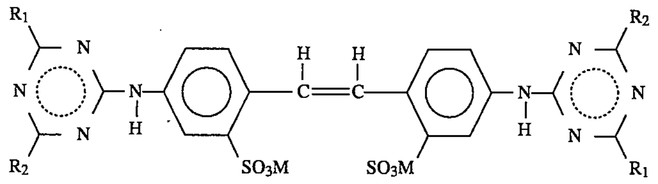

wherein $R_1$ is selected from anilino, N-2-bis-hydroxyethyl and NH2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula $R_1$ is anilino, $R_2$ is N-2-bis-hydroxyethyl and M is a cation such as sodium, the brightener is 4,4,'-bis[(4-anilino-6-(N-2-bis-hydroxyethyl) -s-triazine-2-yl)amino]-2,2'-stilbenedisulfonic acid disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4,'-bis[(4-anilino -6-(N-2-hydroxyethyl-N-methylamino)-s-triazine-2-yl)amino]-2,2'-stilbenedisulfinic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4,'-bis[(4-anilino-6-morphilino-s-triazine-2yl)amino]-2,2'-stilbenedisulfonic acid, sodium salt. This particular brightener species is commercially marketed under the tradename Tinopal AMS-GX by Ciga-Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quickly on these fabrics. The extent to which brighteners deposit on fabrics in the wash solution can be defined by a parameter called the "exhaustion coefficient." The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

E. Optional Detergent Ingredients

The detergent composition of the present invention can also include any number of additional optional ingredients. These include conventional detergent composition components such as suds boosters or suds suppressers, anti-tarnish and anticorrosion agents, soil suspending agents, soil release agents, germicides, pH adjusting agents, non-builder alkalinity sources, chelating agents, smectite clays, enzymes, enzyme-stabilizing agents and perfumes. (See U.S. Pat. No. 3,936,537, issued Feb. 3, 1976 to Baskerville, Jr. et al., the disclosure of which is incorporated herein by reference.)

Additional dye transfer inhibiting agents and additional optical brighteners may also be included. For example, polyvinylpyrrolidone is a suitable dye transfer inhibiting polymer for use in the present detergent composition. Furthermore, additional relatively hydrophobic brighteners optionally may be employed. However, the detergent compositions herein may also be substantially free of hydrophobic brighteners.

Chelating agents are described in U.S. Pat. No. 4,663,071, Bush et al., from Column 17, line 54 through Column 18, line 68, incorporated herein by reference. Suds modifiers are also optional ingredients and are described in U.S. Pat. No. 3,933,672, issued Jan. 20, 1976 to Bartoletta et al., and 4,136,045, issued Jan. 23, 1979 to Gault et al., both incorporated herein by reference. Suitable smectite clays for use herein are described in U.S. Pat. No. 4,762,645, Tucker et al, issued Aug. 9, 1988, Column 6, line 3 through Column 7, line 24, incorporated herein by reference.

While not essential to the detergent composition of the invention, it is preferable to include an enzyme component. Suitable enzyme components are available from a wide variety of commercial sources. For example, suitable enzymes are available from NOVO Industries under product names T-Granulate™ and Savinase™, and Gist-Brocades under product names Maxacal™ and Maxatase™. Included within the group of enzymes are proteases, amylases, lipases, cellulases and mixtures thereof. The enzyme concentration preferably should be from about 0% to about 5%, more preferably from about 0.1% to about 2.5%, and most preferably from about 0.2% to about 1%. Typically, proteases are used at an Activity Unit (Anson Unit) level of from about 0.001 to about 0.05, most preferably from about 0.002 to about 0.02, while amylases are used at an amylase unit level of from about 5 to about 5000, most preferably from about 50 to about 500 per gram of detergent composition.

F. Detergent Composition Formulation

The detergent compositions according to the present invention can be in liquid, paste or granular forms. Such compositions can be prepared by combining the essential and optional components in the requisite concentrations in any suitable order and by an conventional means.

Granular compositions, for example, are generally made by combining base granule ingredients (e.g. surfactants, builders, water, etc.) as a slurry, and spray drying the resulting slurry to a low level of residual moisture (5–12%). The remaining dry ingredients can be admixed in granular powder form with the spray dried granules in a rotary mixing drum and the liquid ingredients (e.g. enzymes, binders and perfumes) can be sprayed onto the resulting granules to form the finished detergent composition. Granular compositions according to the present invention can also be in "compact form", i.e. they may have a relatively higher density than conventional granular detergents, i.e. from 550 to 950 g/l. In such case, the granular detergent compositions according to the present invention will contain a lower amount of "inorganic filler salt", compared to conventional granular detergents; typical filler salts are alkaline earth metal salts of sulphates and chlorides, typically sodium sulphate; "compact" detergents typically comprise not more than 10% filler salt.

Liquid detergent compositions can be prepared by admixing the essential and optional ingredients thereof in any desired order to provide compositions containing components in the requisite concentrations. Liquid compositions according to the present invention can also be in "compact form", in such case, the liquid detergent compositions according to the present invention will contain a lower amount of water, compared to conventional liquid detergents.

G. Fabric Laundering Method

The present invention also provides a method for laundering colored fabrics with little or no dye transfer taking place. Such a method employs contacting these fabrics with an aqueous washing solution formed from an effective amount of the detergent compositions hereinbefore described. Contacting of fabrics with washing solution will generally occur under conditions of agitation.

Agitation is preferably provided in a washing machine for good cleaning. Washing is preferably followed by drying the wet fabric in a conventional clothes dryer. An effective amount of the liquid or granular detergent composition in the aqueous wash solution in the washing machine is preferably from about 500 to about 7000 ppm, more preferably from about 1000 to about 3000 ppm.

EXAMPLES

The following examples illustrate the compositions of the present invention, but are not necessarily meant to limit or otherwise define the scope of the invention.

EXAMPLE I

Several liquid detergent compositions are prepared. The formulation for these compositions are set forth in Table I.

TABLE I

Liquid Detergent Compositions

| Component | Wt. % A | B | C | D |
|---|---|---|---|---|
| $C_{12}$–$C_{15}$ Alkyl sulfate | — | 19.0 | 21.0 | — |
| $C_{12}$–$C_{15}$ Alkyl ethoxylated sulfate | 23.0 | 4.0 | 4.0 | 25.0 |
| $C_{12}$–$C_{14}$ N-methyl glucamide | 9.0 | 9.0 | 9.0 | 9.0 |
| $C_{12}$–$C_{14}$ Fatty alcohol ethoxylate | 6.0 | 6.0 | 6.0 | 6.0 |
| $C_{12}$–$C_{16}$ Fatty acid | 9.0 | 6.8 | 14.0 | 14.0 |
| Citric acid anhydrous | 6.0 | 4.5 | 3.5 | 3.5 |
| Diethylene triamine penta ethylene phosphonic acid (DTPA) | 1.0 | 1.0 | 2.0 | 2.0 |
| Monoethanolamine | 13.2 | 12.7 | 12.8 | 11.0 |
| Propanediol | 12.7 | 14.5 | 13.1 | 10.0 |
| Ethanol | 1.8 | 1.8 | 4.7 | 5.4 |
| Enzymes (protease, lipase, cellulose) | 2.4 | 2.4 | 2.0 | 2.0 |
| Terephtalate-based polymer | 0.5 | 0.5 | 0.5 | 0.5 |
| Boric acid | 2.4 | 2.4 | 2.8 | 2.8 |
| 2-butyl-octanol | 2.0 | 2.0 | 2.0 | 2.0 |
| DC 3421 R(1) FF 400 R(2) | 0.3 | 0.4 | 0.3 | 0.4 |
| Poly(4-vinylpyridine)-N-oxide (PVNO) | — | — | 0.5 | 0.5 |
| N-vinylpyrrolidone/N-vinyl-imidazole copolymer - MW 10,000 (PVPVI) | 0.3 | 0.3 | — | — |
| Tinopal UNPA-GX Brightener | 0.075 | 0.21 | — | — |
| Tinopal 5BM-GX Brightener | — | — | 0.21 | 0.075 |
| Water & minors | up to 100% | | | |

(1)DC 3421 is a silicone oil commercially available from Dow Corning.
(2)is a silicone glycol emulsifier available from Dow Corning.

The compositions described in Table I are suitable for laundering colored fabrics in aqueous washing solution while providing excellent dye transfer inhibition benefits. Dye transfer inhibition performance provided by the combination of the PVNO or PVPVI and the selected Tinopal brightener is significantly better than if the dye transfer inhibiting polymers or the optical brighteners were used alone. Dye transfer inhibition performance for these compositions is also superior to that which would be provided if other conventional relatively hydrophilic optical brighteners were to be substituted for the Tinopal brighteners employed.

EXAMPLE II

Concentrated built heavy duty liquid detergent compositions are prepared having the formulations set forth in Table II.

TABLE II

Liquid Detergent Compositions

| Component | Wt. % A | B |
|---|---|---|
| $C_{14-15}$ Alkyl polyethoxylate (2.25) sulfonic acid | 23.00 | 12.50 |
| $C_{12-13}$ Linear alkyl benzene sulfonic acid | — | 11.46 |
| 1,2 Propanediol | 10.50 | 3.97 |
| Monoethanolamine | 12.50 | 3.65 |
| $C_{12-13}$ Alkyl polyethoxylate (6.5) | 6.00 | 1.78 |
| Ethanol | 3.80 | 1.75 |
| Polyhydroxy $C_{12-14}$ fatty acid amide | 9.00 | — |
| $C_{12-14}$ Coconut fatty acid | 9.00 | 2.60 |
| Citric acid | 6.00 | 6.04 |
| DTPA | 0.95 | — |
| Sodium formate | 0.14 | — |
| Boric acid | 2.4 | 1.0 |
| Tetraethylenepentaaniine ethoxylate (15–18) | 1.00 | 1.44 |
| Soil release polymer | 0.46 | — |
| Enzymes (protease, lipase, cellulose) | 2.55 | 2.27 |
| Silicone antifoam composition | 0.04 | 0.02 |
| Poly(4-vinylpyridine)-N-oxide (PVNO) | 0.10 | 0.10 |
| Brightener - Tinopal UNPA-GX | 0.20 | 0.20 |
| Water and miscellaneous minors | Balance to 100% | |

The liquid detergent compositions of Table II have dye transfer inhibition performance characteristics which are substantially similar to those of Table I compositions.

EXAMPLE III

Several compact granular detergent compositions are prepared. The formulations for these compositions are set forth in Table III.

TABLE III

| Granular Detergent Compositions | | | |
|---|---|---|---|
| | Wt. % | | |
| Component | A | B | C |
| $C_{11}$-$C_{14}$ Linear alkyl benzene sulfonate | 11.40 | — | — |
| $C_{12}$-$C_{15}$ Alkyl alkoxylated sulfate | — | 10.00 | — |
| $C_{12}$-$C_{14}$ N-methyl glucamide | — | — | 13.00 |
| Tallow alkyl sulfate | 1.80 | 1.80 | 1.80 |
| $C_{45}$ alkyl sulfate | 3.00 | 3.00 | 3.00 |
| $C_{45}$ alcohol 7 times ethoxylated | 4.00 | 4.00 | 4.00 |
| Tallow alcohol 11 times ethoxylated | 1.80 | 1.80 | 1.80 |
| Dispersant | 0.07 | 0.07 | 0.07 |
| Silicone fluid | 0.80 | 0.80 | 0.80 |
| Trisodium citrate | 14.00 | 14.00 | 14.00 |
| Citric acid | 3.00 | 3.00 | 3.00 |
| Zeolite | 32.50 | 32.50 | 32.50 |
| Maleic acid acrylic acid copolymer | 5.00 | 5.00 | 5.00 |
| Cellulose (actve protein) | 0.03 | 0.03 | 0.03 |
| Alkalase/BAN | 0.60 | 0.60 | 0.60 |
| Lipase | 0.36 | 0.36 | 0.36 |
| Sodium silicate | 2.00 | 2.00 | 2.00 |
| Sodium sulfate | 3.50 | 3.50 | 3.50 |
| Poly(4-vinylpyridine)-N-oxide (PVNO) | 0.10 | 0.10 | — |
| N-vinylpyrrolidone/N-vinylimidazole copolymer - MW 10,000 (PVPVI) | — | — | 0.20 |
| Brightener - Tinopal UNPA-GX | 0.20 | — | 0.20 |
| Brightener - Tinopal 5BM-GX | — | 0.20 | — |
| Misc. (water, minors, etc) | Balance to 100% | | |

The compositions described in Table III are suitable for laundering colored fabrics in aqueous solutions while providing excellent dye transfer inhibition benefits. Dye transfer inhibition performance provided by the combination of the PVNO or PVPVI and the selected Tinopal brighteners is significantly better than if the dye transfer inhibiting polymers or the optical brighteners were used alone. Dye transfer inhibition performance for these compositions is also superior to that which would be provided if other conventional relatively hydrophilic optical brighteners were to be substituted for the Tinopal brighteners employed.

EXAMPLE IV

A concentrated heavy duty granular detergent product is prepared having the composition set forth in Table IV.

TABLE IV

| Compact Granular Detergent | |
|---|---|
| Component | Wt. % |
| $C_{14-15}$ Alkyl ethoxy sulfonic acid | 5.44 |
| $C_{12-13}$ Linear alkyl sulfonic acid | 12.70 |
| $C_{12-14}$ Alkyl ethoxylate | 0.50 |
| Alumino silicate (76%) | 25.40 |
| Polyacrylate | 3.12 |
| Tinopal UNPA-GX brightener | 0.27 |
| PEG-8000 (50%) | 1.53 |
| SUicone suds suppressor | 0.02 |
| Enzymes | 1.29 |
| Citric acid | 3.50 |
| Perborate | 2.00 |
| PVNO | 0.10 |
| Moisture/sodium sulfate/aesthetics/$NaCO_3$/ minors, unreacted material | Balance to 100% |

The granular detergent composition of Table IV has dye transfer inhibition performance characteristics which are substantially similar to those of the Table III compositions.

What is claimed is:

1. A laundry detergent composition that provides especially effective inhibition of dye transfer between fabrics being laundered in aqueous washing solutions formed from such a composition, which composition comprises:

(a) from about 1% to about 80% of a detersive surfactant;

(b) from about 0.1% to about 80% of detergent builder component;

(c) from about 0.01% to 10% by weight of a polymeric dye transfer inhibiting agent selected from the group consisting of polyamine N-oxide polymers, copolymers and N-vinylpyrrolidone and N-vinylimidazole and combinations of said polymers and copolymers; and (d) from about 0.005% to 5% by weight of a hydrophilic optical brightener having the formula:

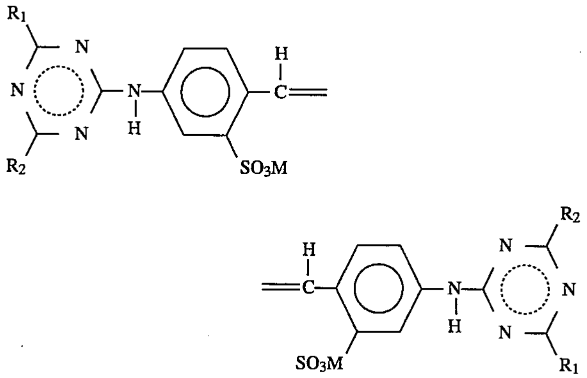

wherein $R_1$ is selected from the group consisting of anilino, N-2-bis-hydroxyethyl and NH-2-hydroxyethyl; $R_2$ is selected from the group consisting of N-2-bis-hydroxyethyl, N-2-hydroxyethyl-N-methylamino, morphilino, chloro and amino; and M is a salt-forming cation.

2. A detergent composition according to claim 1 wherein (a) the detersive surfactant is selected from the group consisting of anionic surfactants, nonionic surfactants and combinations thereof;

(b) the builder is selected from the group consisting of aluminosilicates, crystalline layered silicates, citrates and combinations thereof;

(c) the polymeric dye transfer inhibiting agent is a polyvinylpyridine N-oxide; and (d) the hydrophilic optical brightener is 4,4'-bis[(4-anilino-6-(N-2-bis-hydroxyethyl)-s-triazine-2yl)amino]-2,2'-stilbenedisulfonic acid disodium salt.

3. A composition according to claim 2 wherein the polyvinylpyridine N-oxide has an amine to amine N-oxide molar ratio of from about 3:1 to 1:1,000,000 and an average molecular weight of from about 1,000 to 500,000.

4. A composition according to claim 1 wherein (a) the detersive surfactant is selected from the group consisting of anionic surfactants, nonionic surfactants and combinations thereof;

(b) the builder is selected from the group consisting of aluminosilicates, crystalline layered silicates, citrates and combinations thereof;

(c) the polymeric dye transfer inhibiting agent is a copolymer of N-vinylpyrrolidone and N-vinylimidazole having a molar ratio of N-vinylpyrrolidone to N-vinylimidazole of from about 0.8:1 to 0.3:1 and an average molecular weight of from about 5,000 to 200,000; and (d) the hydrophilic optical brightener is 4,4'-bis[(4-anilino-6-(N- 2-bis-hydroxyethyl)-s-triazine- 2yl)amino]-2,2'-stilbenedisulfonic acid disodium salt.

5. A composition according to claim 4 where the dye transfer inhibiting copolymer has a molar ratio of N-vinylpyrrolidone to N-vinylimidazole of from about 0.6:1 to 0.4:1 and an average molecular weight of from about 10,000 to 20,000.

6. A liquid laundry detergent composition that provides especially effective inhibition of dye transfer between fabrics and being laundered in aqueous washing solutions formed from such a composition, which composition comprises:

(a) from about 5% to 50% by weight of a detersive surfactant selected from the group consisting of i) sodium, potassium and ethanolamine alkylsulfates wherein the alkyl group contains from 10 to 22 carbon atoms;

ii) sodium, potassium and ethanolamine alkylpolyethoxylate sulfates wherein the alkyl group contains from 10 to 22 carbon atoms and the polyethoxylate chain contains from 1 to 15 ethylene oxide moieties;

iii) polyhydroxy fatty acid amides of the formula

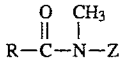

wherein R is a $C_{9-17}$ alkyl or alkenyl and Z is glycityl derived from a reduced sugar or alkoxylated derivatives thereof;

iv) alcohol ethoxylates of the formula $R^1(OC_2H_4)_nOH$ where $R^1$ is a $C_{10}$–$C_{16}$ alkyl group or a $C_8$–$C_{12}$ alkyl phenyl group and n is from about 3 to 80; and (b) from about 1% to 10% by weight of a detergent builder component selected from the group consisting of carboxylate and polycarboxylate builders;

(c) from about 0.05% to 0.5% by weight of a polymeric dye transfer inhibiting agent selected from the group consisting of i) polyamine N-oxides having an anionic to amino N-oxide molar ratio of from about 10:1 to 1:1,000,000 and having an average molecular weight of from about 500 to 1,000,000; and ii) polymers of N-vinylpyrrolidone and N-vinylimidazole having a molar ratio of N-vinylimidazole to N-vinylpyrrolidone of from about 1:1 to 0.2:1 and having an average molecular weight of from about 5,000 to 1,000,000; and (d) from about 0.01% to 1% of a hydrophilic optical brightener selected from the group consisting of i) 4,4'-bis[(4-anilino-6-(N-2-bis-hydroxyethyl)-s-triazine-2yl)amino]-2,2'-stilbenedisulfonic acid disodium salt;

ii) 4,4'- bis[(4-anilino-6-(N-2 -hydroxyethyl-N-methylamino)-s-triazine-2-yl)amino]-2,2'-stilbenedisulfonic acid disodium salt; and iii) 4,4'-bis[(4-anilino-6-morphilino-s-triazine-2-yl)amino]-2,2'-stilbenedisulfonic acid, sodium salt.

7. A liquid detergent composition according to claim 6 wherein a) the dye transfer inhibiting agent is poly(4-vinylpyridine-N-oxide) having an amine to amine N-oxide ratio of about 1:10 and an average molecular weight of about 10,000; and b) the optical brightener is Tinopal UNPA-GX.

8. A liquid detergent composition according to claim 6 wherein a) the dye transfer inhibiting agent is a copolymer of N-vinylpyrrolidone and N-vinylimidazole having an N-vinylpyrrolidone to N-vinylimidazole molar ratio of from about 0.6:1 to 0.4:1 and an average molecular weight of from about 10,000 to 20,000; and b) the optical brightener is Tinopal UNPA-GX.

9. A liquid detergent composition according to claim 6 which also comprises from about 0.1% to 2.5% by weight of an enzyme component selected from the group consisting of proteases, lipases, amylases, cellulases and combinations of said enzymes.

10. A granular laundry detergent composition that provides especially effective inhibition of dye transfer between fabrics being laundered in aqueous washing solutions formed from such a composition, which composition comprises:

(a) from about 5% to 50% by weight of a detersive surfactant selected from the group consisting of i) sodium and potassium alkylpolyethoxylate sulfates wherein the alkyl group contains from 10 to 22 carbon atoms and the polyethoxylate chain contains from 1 to 15 ethylene oxide moieties;

ii) sodium and potassium C9 to C15 alkyl benzene sulfonates;

iii) sodium and potassium C8 to C18 alkyl sulfates;

iv) polyhydroxy fatty acid amides of the formula

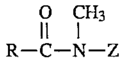

wherein R is a $C_{9-17}$ alkyl or alkenyl and Z is a glycityl derived from a reduced sugar or alkoxylated derivatives thereof; and v) combinations of these surfactants;

(b) from about 1% to 50% by weight of a detergent builder selected from the group consisting of sodium carbonate, sodium silicate, crystalline layered silicates, aluminosilicates, oxydisuccinates and citrates;

(c) from about 0.05% to 0.5% by weight of a polymeric dye transfer inhibiting agent selected from the group consisting of i) polyamine N-oxides having an anionic to amine N-oxide molar ratio of from about 10:1 to 1:1,000,000 and having an average molecular weight of from about 500 to 1,000,000; and ii) copolymers of N-vinylpyrrolidone and N-vinylimidazole having a molar ratio of N-vinylimidazole to N-vinylpyrrolidone of from about 1:1 to 0.2:1 and having an average molecular weight of from about 5,000 to 1,000,000; and (d) from about 0.01% to 1% of a hydrophilic optical brightener selected from the group consisting of i) 4,4'-bis[(4-anilino-6-(N-2-bis-hydroxyethyl)-s-trizine-2yl)amino]-2,2'-stilbenedisulfonic acid disodium salt;

4,4'-bis[(4-anilino-6-(N-2-hydroxyethyl-N-methylamino)-s-trizine-2-yl)amino]-2,2'-stilbenedisulfonic acid disodium salt; and iii) 4,4'-bis[(4-anilino-6-morphilino-s-trizine-2yl)amino]-2,2'-stilbenedisulfonic acid, sodium salt.

11. A granular detergent composition according to claim 10 wherein a) the dye transfer inhibiting agent is poly(4-vinylpyridine-N-oxide) having an amine to amine N-oxide ratio of about 1: 10 and an average molecular weight of about 10,000; and b) the optical brightener is Tinopal UNPA-GX.

12. A granular detergent composition according to claim 10 wherein a) the dye transfer inhibiting agent is a copolymer of N-vinylpyrrolidone and N -vinylimidazole having an N-vinylpyrrolidone to N-vinylimidazole molar ratio of from about 0.6:1 to 0.4:1 and an average molecular weight of from about 10,000 to 20,000; and b) the optical brightener is Tinopal UNPA-GX.

13. A granular detergent composition according to claim 10 which also comprises from about 0.1% to 2.5% by weight of an enzyme component selected from the group consisting of proteases, lipases, amylases, cellulases and combinations of said enzymes.

14. A method for cleaning colored fabrics in the wash with little or no dye transfer between fabrics, said method comprising contacting said fabrics with a wash solution which contains an effective amount of a detergent composition according to claim 1.

15. A method according to claim 14 wherein the detergent composition used comprises PVNO and Tinopal UNPA-GX brightener.

16. A method for cleaning colored fabrics in the wash with little or no dye transfer between fabrics, said method comprising contacting said fabrics with a wash solution which contains an effective amount of a detergent composition according to claim 6.

17. A method according to claim 16 wherein the detergent composition used comprises PVNO and Tinopal UNPA-GX brightener.

18. A method for cleaning colored fabrics in the wash with little or no dye transfer between fabrics, said method comprising contacting said fabrics with a wash solution which contains an effective amount of a detergent composition according to claim 10.

19. A method according to claim 18 wherein the detergent composition used comprises PVNO and Tinopal UNPA-GX brightener.

* * * * *